United States Patent [19]

Barthel et al.

[11] Patent Number: 5,415,158
[45] Date of Patent: May 16, 1995

[54] FLEXIBLE ENDOSCOPE WITH FORCE LIMITING SPRING COUPLER

[75] Inventors: Thomas C. Barthel, Becker; Rocky R. Campbell, Maple Plain; Craig L. Riedl, Long Lake, all of Minn.

[73] Assignee: Clarus Medical Systems, Inc., Minneapolis, Minn.

[21] Appl. No.: 75,868

[22] Filed: Jun. 11, 1993

[51] Int. Cl.6 .............................................. A61B 1/00
[52] U.S. Cl. ........................................ 128/4; 128/6; 604/95
[58] Field of Search .......................... 128/4, 6, 7, 772; 138/118, 120; 604/95; 606/46

[56] References Cited

U.S. PATENT DOCUMENTS

| | | |
|---|---|---|
| 4,294,233 | 10/1981 | Takahashi . |
| 4,483,326 | 11/1984 | Yamaka et al. . |
| 4,602,620 | 7/1986 | Marx ................................ 128/77 |
| 4,665,257 | 4/1987 | Iwashita . |
| 4,762,118 | 8/1988 | Lia et al. . |
| 4,762,119 | 8/1988 | Allred, III et al. . |
| 4,770,163 | 9/1988 | Ono et al. ............................ 128/6 |
| 4,787,369 | 11/1988 | Allred, III et al. . |
| 4,941,454 | 7/1990 | Wood et al. . |
| 4,996,974 | 3/1991 | Ciareli . |
| 5,025,804 | 6/1991 | Kondo . |
| 5,127,393 | 7/1992 | McFarlin et al. . |
| 5,275,151 | 1/1994 | Sholkey et al. ........................ 128/4 |

FOREIGN PATENT DOCUMENTS 2161725 1/1986 United Kingdom .................... 128/4

*Primary Examiner*—Richard J. Apley
*Assistant Examiner*—Beverly A. Meindl
*Attorney, Agent, or Firm*—Haugen and Nikolai

[57] ABSTRACT

A flexible endoscope have a force limiting coupler. The endoscope comprises an elongated tubular member having a proximal end, a distal end and a wall defining a lumen extending there through. A handle member is fixed to the proximal end of the tubular member. The handle member has a slidable knob member which is coupled to a force limiting means to limit the travel of the knob member. A deflection wire is coupled at one end to the force limiting means and a second end to the distal end of the tubular member. The force limiting means has a predetermined spring constant. The distal end of the endoscope can be deflected in finer increments and acts to preclude potentially damaging forces to be applied to the endoscope or to tissue.

8 Claims, 2 Drawing Sheets

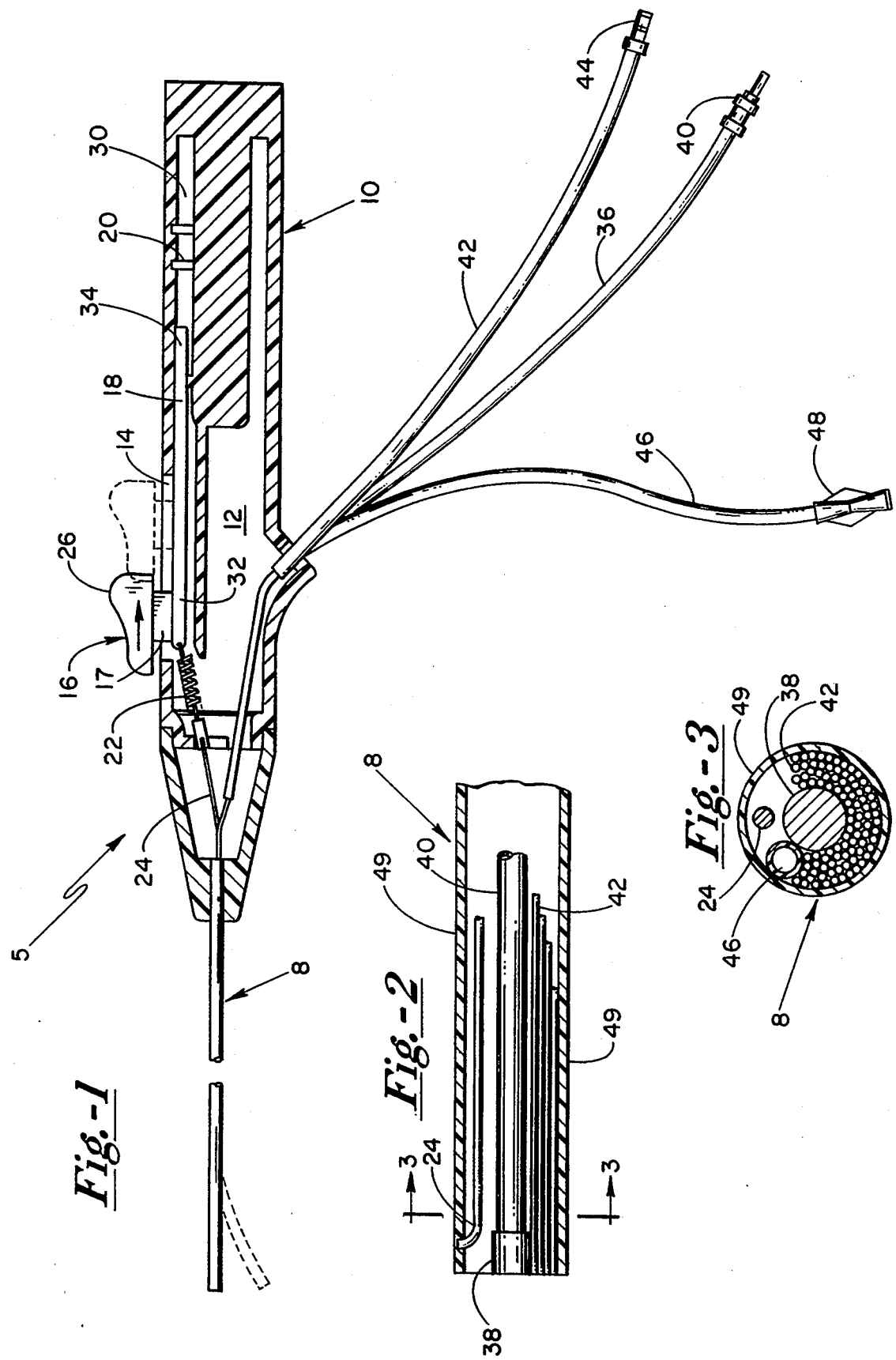

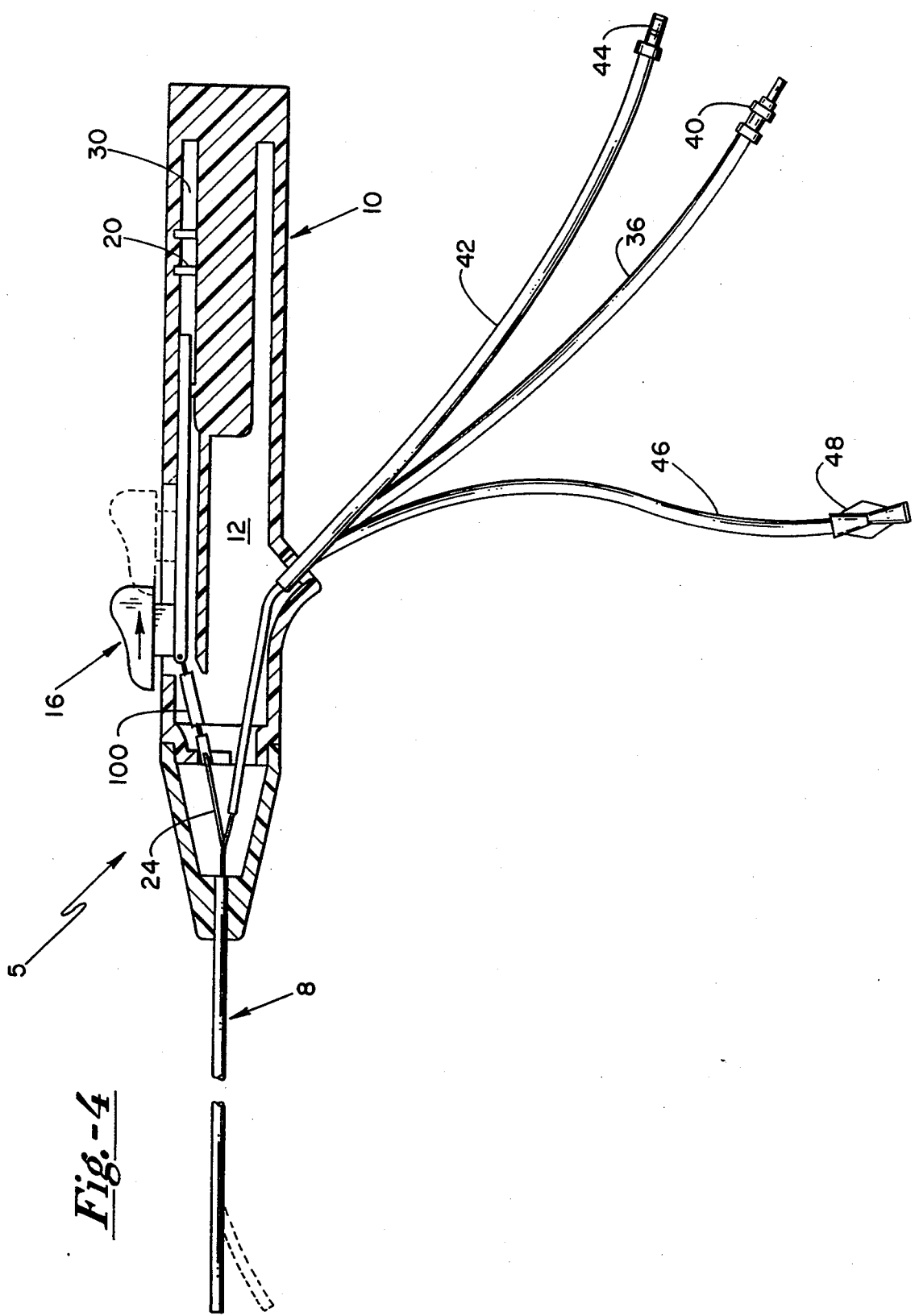

FLEXIBLE ENDOSCOPE WITH FORCE LIMITING SPRING COUPLER

I. FIELD OF INVENTION

This invention relates generally to medical apparatus for diagnosing and treating abnormalities in internal body organs, and more particularly to a flexible endoscope having a force limiting spring coupler allowing greater control over deflection of the endoscope distal end.

II. BACKGROUND OF THE INVENTION

Endoscopes are used in a variety of medical procedures to see inside the body. Rather than make a large incision and expose the surgical site to view, various types of endoscopes are used which are designed to be inserted into the body through a natural orifice or through a substantially smaller puncture or incision. Many forms of endoscopes are known in the art. They generally comprise an elongated multiple lumen tube having a proximal end and a distal end. Included among the plural lumens is one containing an optical fiber or bundle of such fibers for transmitting light from a light source coupled to the proximal end of the tube to the distal tip for illuminating the vessel or organ cavity to be examined. Another lumen is typically used to contain a further optical fiber for transmitting the illuminated image to an eye piece or other viewing device coupled to the proximal end of the endoscope. An endoscope will further typically include a lumen comprising a working channel through which flushing liquid may be injected and aspirated. The working channel may also provide a pathway through which other instruments may be passed through to the location where the treatment is to be affected.

Rigid endoscopes, without tools or working channels, can be used strictly to monitor a surgical procedure. Typical of such devices are laparoscopes, such as is used during laparoscopic cholecystectomy procedures. The laparoscope is inserted through a small puncture wound in the abdominal wall and various other cannulae or tubes are likewise inserted allowing cutting or grasping instruments to be introduced through the lumen of these cannulae. The surgical field is observed on a display device (TV monitor) coupled to the laparoscope. The optical system employed in the rigid endoscopes does not allow the endoscope to be bent and this necessarily limits the ability of surgeon to gain access to many areas of the body to be worked on.

A flexible deflectable endoscope, on the other hand, provides access to areas of the body that are only accessible through tortuous, curved passages. Incorporating a working channel in a flexible deflectable endoscope allows the surgeon to pass a flexible tool through the channel to manipulate tissue at the distal end of the endoscope.

There are two types of flexible deflectable endoscopes. One type is passively deflectable, being bent by curved passages or other tissue. The other type is actively deflectable. Actively deflectable endoscopes are mechanically activated by the physician. The physician deflects the endoscope by means of one or more pull wires located inside the endoscope tube. These pull wires are anchored near the distal tip of the tube and they are free to move within the endoscope for the remainder of its length. The proximal end of the endoscope tube is held securely in a hand piece. When the wires at the proximal end are pulled such as by actuating a thumb slide member, the distal tip of the endoscope deflects. The further the wire is tensioned, the more the distal tip deflects. As endoscopes have become smaller, structural strength limits are more easily reached, making a force limiting feature desirable. The problem created by the smaller endoscope is that the user may exert excessive force on the endoscope tip during deflection. Tissue can be damaged if this excessive force occurs when the endoscope tip is bound by body tissue. The user can also damage the endoscope if excessive force is exerted on the endoscope tip during deflection if the endoscope tip is within a rigid cannula.

To overcome these potential problems, the present invention adds a force limiting coupler such as an elastomeric band or a tension spring to the proximal end of the deflection wire where it joins to the thumb slide actuator. The invention also includes a backstop to limit the amount of travel of the deflection wire. As the thumb slide is pulled back toward the proximal end of the hand piece, it pulls on the force limiting coupler, which in turn pulls on the deflection wire. The addition of the force limiting coupler allows the user to deflect the distal end of the endoscope in finer increments and acts to preclude potentially damaging forces to be applied to the endoscope or to tissue.

SUMMARY OF THE INVENTION

The present invention is an endoscope having a force limiting coupler used to limit the travel of the endoscope tip when deflected and to limit the maximum force that can be transmitted to the tip of an actively deflectable endoscope. In accordance with the present invention, there is provided an elongated tubular member having an internal lumen extending from a proximal end to a distal end of the tubular member. This lumen is designed to accommodate optical fibers or a light pipe. The optical fibers transmit light from the proximal end to the distal end. Located at the distal end is a lens for transmitting the image being viewed at the distal end of the endoscope back to a viewing device coupled to the proximal end thereof. The lumen may also accommodate a working channel for receiving surgical tools or an irrigation channel for receiving a flushing fluid.

A handle member is fixed to the proximal end of the tubular member. The handle member has interior cavity and a slit connecting the interior cavity with the outside of the handle member. A slidable knob is received in the handle slit and is coupled to a force limiting coupler, such as a spring or an elastomeric band. A deflection wire is coupled to the force limiting coupler opposite the slidable knob and extends through the length of the flexible tube. The deflection wire is anchored in the lumen wall at the distal end of the flexible tubular member. The handle cavity for receiving the slidable knob has a factory set backstop for limiting the range of movement of the knob.

Deflection to the distal end of the flexible tubular member is caused manually by sliding the thumb slide knob towards the proximal end of the handle which, in turn, tensions the force limiting coupler and tightens the deflection wire. The deflection of the endoscope tip is limited by the coupler and length of travel of the knob within the handle slit. Furthermore, the coupler allows greater control over the amount of deflection because, with the coupler, the knob must be moved a larger distance than without the coupler for the same amount of deflection.

DESCRIPTION OF THE DRAWINGS

Further details, objects and advantages of the invention will become apparent to those skilled in the art from the following detailed description of a preferred embodiment in which like numerals in the several views refer to corresponding parts.

FIG. 1 is a cross-sectional view of the side elevation of the present invention showing the deflected position in broken line;

FIG. 2 is an enlarged cross-sectional view of the side elevation of the distal end of the present invention; and FIG. 3 is a cross-section of the flexible tubular member taken along line 3—3 of FIG. 1.

FIG. 4 is a cross-sectional side view of the handle of an alternative embodiment.

DESCRIPTION OF THE PREFERRED EMBODIMENT

Referring first to FIG. 1, there is shown a sectioned side elevation view of the endoscope with a force limiting spring coupler in accordance with the present invention. The endoscope 5 comprises flexible tubular member indicated generally by 8 and a handle member, indicated generally as 10, affixed to a proximal end of said tubular member 8. The handle member has an interior cavity 12 and a slit 14 extending from the exterior of the handle into the interior cavity 12. A moveable knob 16 has its stem 17 received in the slit 14 for reciprocal movement within the slit 14. The stem 17 is joined to a rigid rod 18 for engaging a back stop 20 member located in the slide receiving groove in the handle interior. A force limiting spring, such as tension spring 22, is coupled at one end to the slide rod member 18 and at the other end to a deflection wire 24. The deflection wire 24 is firmly anchored to the distal end of the endoscope tubular member 8 and is free to slide inside the tubular member 8.

The knob 16 and the stem 17 to which it is attached are slidably mounted within the slit 14. The knob 16 includes a serrated thumb engageable exterior portion 26. The rigid slide rod 18 is received in an elongated narrow groove 30 located in the cavity 12. The backstop 20 is located in this elongated groove 30. The rod 18 has a first end 34 for engaging the backstop 20 and a second end 32 coupled to the force limiting spring coupler 22. The second end 32 is also coupled by the stem 17 to the thumb knob 16. The other end of the force limiting spring 22 is, in turn, coupled to the deflection wire 24. It can be appreciated from FIG. 1 that the backstop 20 limits the amount of travel in the proximal direction of the slide rod 28.

The handle cavity also receives an image fiber carrying a bundle 36 comprising 6,000 to 15,000 optical fibers which serve to carry an image of a subject on which an objective lens 38 (FIG. 2) is focused. A connector 40 of standard construction connects the image fiber 36 to a magnifier/viewing system. The magnifying/viewing system will enlarge the image, which is commonly displayed on a TV monitor 30. A further optical rod or bundle of fibers 42 for carrying the light from a light source to the distal end of the tube is also shown. It has a connector 44 facilitating connecting the lumination fibers 42 to a light source. Lastly, the handle may accommodate a suction/irrigation tube 46. The connector 48 is used to couple the irrigating tube to a fluid source used to flush the blood out of the view of the endoscope and to keep the optical system clean.

Turning now to FIGS. 2 and 3, an enlarged view of the distal end of the tubular member 8 is shown. As can be seen, the deflection wire 24 is anchored firmly in the wall 49 of the tubular member 8 at the distal end. An objective lens 38 is located at or near the distal end of the endoscope. This lens 38 will create an image of the area where the endoscope light is directed. The image will then appear on the front face of the image fiber bundle 40 and when connected to a viewing system may be displayed. A typical diameter of an objective lens is 0.5 mm. The image fiber bundle 40 is shown operatively connected to the objective lens 38. The plurality of illumination fibers 42 are located around the lower portion of the objective lens 38 in this embodiment.

When used in a medical procedure, the flexible endoscope is inserted into the body through a natural orifice, a surgically created orifice or a cannula. Light is transmitted from the distal end of the tubular member 8 through the optical fibers 42 located in the tubular member 8. The optical lens 38 picks up the image and all the while the endoscope is being positioned, the surgeon is able to view the image picked up by the fiber optic media in the lumen either through an eyepiece or by way of a video camera and display terminal which is joined to the connector 40.

When the need arises to deflect the tip of the endoscope, the user manipulates the slidable knob 16 by pulling it back towards the proximal end of the handle member. The broken line in FIG. 1 shows the position of the knob 16 and endoscope tip in a deflected position. The knob 16 pulls on the spring 22 which, in turn, pulls on the deflection wire 24. The length of travel of the knob 16 is limited by a transversely extending the backstop 20 whose location is preset during manufacture.

The force limiting coupler has a predetermined spring constant relating force to deflection. The spring constant affects the amount of deflection which will occur as knob 16 moves in the slit 14. For example, if the backstop 20 limits the travel of the knob 16 to 0.5 inches and the spring 22 has a rate of 2.0 pounds per inch of extension, then the maximum force that can be applied is 1 pound. Thus a spring of suitable characteristics can be used to limit the maximal transmitted force. For example, if deflection of the tip is desired to be at 40 degrees, the deflection knob 16 need only be moved 0.05 inches if there is no spring. If a spring is used, a spring rate of 2 pounds per inch of extension allows the deflection knob 16 to be moved ½ inch to result in the 45 degrees deflection of tip. It can be readily seen that the use of the spring coupling and the backstop eliminates exerting excessive force on the endoscope tip when the deflection knob 16 is manipulated. The user also has greater control over the amount of deflection because the knob must be moved a greater distance with the force limiting coupler than without it for the same amount of deflection. This allows the user to make fine adjustments of the deflection. It also prevents the user from deflecting the tip too much.

In an alternative embodiment, the force limiting coupler can be an elastomeric band instead of a spring. As shown in FIG. 4, an elastomeric band 100 is coupled at a first end to deflection wire 124 and at a second end to the slidable knob 116. The endoscope assembly is otherwise identical to the embodiment of FIG. 1 and operates in the same fashion.

This invention has been described herein in considerable detail in order to comply with the patent statutes and to provide those skilled in the art with the information needed to apply the novel principals and to construct and use specialized components as are required. However, it is to be understood that the invention can be carried out by specifically different equipment and devices, and that various modifications, both as to the equipment details and operating procedures can be accomplished without departing from the scope of the invention itself.

What is claimed:

1. An endoscope having a force limiting coupler, said endoscope comprising:
   a. an elongated tubular member having a proximal end, a distal end, and a wall defining a lumen extending therethrough;
   b. a slidable knob member;
   c. a handle member fixed to said proximal end of said tubular member, said handle member having an elongated slit formed therein for receiving said slidable knob member;
   d. a resilient force limiting means coupled to said slidable knob member for limiting longitudinal travel of said slidable knob member and for limiting deflection of said distal end of said elongated tubular member whereby longitudinal travel of said slidable knob member gives greater control over the deflection of said distal end of said elongated tubular member; and
   e. a deflection wire having a proximal end and a distal end, said deflection wire's proximal end being coupled to said resilient force limiting means and said deflection wire's distal end being anchored to said wall of said lumen at said distal end of said elongated tubular member.

2. An endoscope having a force limiting coupler, said endoscope comprising:
   a. an elongated tubular member having a proximal end, a distal end, and a wall defining a lumen extending therethrough;
   b. a slidable knob member;
   c. a handle member fixed to said proximal end of said tubular member, said handle member having an elongated slit formed therein for receiving said slidable knob member;
   d. a resilient member of a predetermined spring constant coupled to said slidable knob member for limiting longitudinal travel of said slidable knob member and for limiting deflection of said distal end of said elongated tubular member whereby longitudinal travel of said slidable knob member gives greater control over the deflection of said distal end of said elongated tubular member; and
   e. a deflection wire having a proximal end and a distal end, said deflection wire's proximal end being coupled to said resilient force limiting means and said deflection wire's distal end being anchored to said wall of said lumen at said distal end of said elongated tubular member.

3. An endoscope of claim 2 wherein said slidable knob member has a predetermined fixed range of travel.

4. An endoscope of claim 2 wherein the resilient member is a tension spring.

5. An endoscope of claim 2 wherein the resilient member is an elastomeric band.

6. An endoscope of claim 2 further including:
   a. An illumination fiber means extending through said lumen for illuminating an area proximate said distal end of said elongated tubular member;
   b. An objective lens means for creating an image proximate said distal end of said elongated tubular member; and
   c. An image fiber extending through said lumen operatively connected at a first end to said objective lens and operatively connected at a second end to a monitor means for viewing said image.

7. An endoscope of claim 2 further including an irrigation channel means extending through said lumen for flushing at said distal end of said elongated tubular member.

8. An endoscope of claim 2 further including a stop located in said elongated slit for limiting the longitudinal travel of said slidable knob member.

* * * * *